(12) United States Patent
Wang

(10) Patent No.: US 8,445,249 B2
(45) Date of Patent: *May 21, 2013

(54) SSO7-POLYMERASE CONJUGATE PROTEINS

(75) Inventor: Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/705,438

(22) Filed: Feb. 12, 2010

(65) Prior Publication Data

US 2010/0279360 A1 Nov. 4, 2010

Related U.S. Application Data

(63) Continuation of application No. 10/280,139, filed on Oct. 23, 2002, now Pat. No. 7,666,645.

(51) Int. Cl.
*C12N 9/12* (2006.01)
*C07K 1/00* (2006.01)

(52) U.S. Cl.
USPC .......... 435/194; 435/183; 435/69.1; 435/455; 530/350; 530/358

(58) Field of Classification Search
None
See application file for complete search history.

(56) References Cited

U.S. PATENT DOCUMENTS 5,972,603 A 10/1999 Bedford et al.
6,228,628 B1 5/2001 Gelfand et al.

FOREIGN PATENT DOCUMENTS

WO    WO 01/92501 A1    12/2001

OTHER PUBLICATIONS

Agback, Peter, et al.; "Architecture of Nonspecific Protein-DNA Interactions in the Sso7d-DNA Complex;" *Nature Structural Biology*; Jul. 1998; pp. 579-584; vol. 5; No. 7.
Baumann, Herbert, et at.; "DNA-Binding Surface of the Sso7d Protein from *Sulfolobus solfataricus;*" *J. Mol. Biol.*; 1995; pp. 840-846; vol. 247; Academic Press Limited.
Catanzano, Francesca, et al.; "Differential Scanning Calorimetry Study of the Thermodynamic Stability of Some Mutants of Sso7d from *Sulfolobus solfataricus;*" *Biochemistry*; 1998; pp. 10493-10498; vol. 37; No. 29; American Chemical Society.
Consonni, R., et al., "A single-point mutation in the extreme heat- and pressure-resistant sso7d protein from *Sulfolobus solfataricus* leads to a major rearrangement of the hydrophobic core," 1999, Biochemistry, American Chemical Society, vol. 38, 12709-12717.
Gao, Y-G, et al., "The crystal structure of the hyperthermophile chromosomal protein SS07D Bound to DNA," *Nature Structural Biology*, vol. 5(9), pp. 782-786 (1998).
Gao, Yi-Gui, et al.; "The Crystal Structure of the Hyperthermophile Chromosomal Protein Sso7d Bound to DNA;" *Nature Structural Biology*; Sep. 1998; pp. 782-786; vol. 5; No. 9.
Ngo et al., Computational Complexity, Protein Structure Prediction, and the Levinthal Paradox, in the Protein Folding Problem and Tertiary Structure Prediction, 1994, Merz et al. (ed.), Birkhauser, Boston, MA, pp. 433 and 492-495.
Wang et al., "A novel strategy to engineer DNA polymerases for enhanced processivity and improved performance in vitro," 2004, Nucleic Acids Research, vol. 32, pp. 1197-1207.

*Primary Examiner* — Richard Hutson
(74) *Attorney, Agent, or Firm* — Kilpatrick Townsend & Stockton LLP

(57) ABSTRACT

This invention provides Sso7-polymerase conjugates that exhibit improved activity in a polymerase reaction.

17 Claims, 2 Drawing Sheets

FIGURE 2

```
          10                    20                    30
Sso7d  AT VKFKYKGEEKEVD I SKIKKVWRVGKMISFTY
Sac7e  AK VRFKYKGEEKEVD T SKIKKVWRVGKMVSFTY
       A  V.FKYKGEEKEVD   SKIKKVWRVGKM.SFTY 40              50              60
Sso7d  DEG GGKTGRGAVSEKDAPKEL LQ ML E KQ K K
Sac7   DDN G-KTGRGAVSEKDAPKEL MD ML A RA E KKK
e      D   GGKTGRGAVSEKDAPKEL    ML         KKK
```

US 8,445,249 B2

SSO7-POLYMERASE CONJUGATE PROTEINS

CROSS-REFERENCE TO RELATED APPLICATIONS

This application is a continuation of co-pending U.S. patent application Ser. No. 10/280,139, filed Oct. 23, 2002, which application is herein incorporated by reference.

BACKGROUND OF THE INVENTION

The activity of a polymerase can be improved by joining a sequence-non-specific double-stranded nucleic acid binding domain to the enzyme, or its catalytic domain (see, e.g., WO0192501). Such modified polymerases exhibit increased processivity in comparison to the unmodified enzymes. In some instances, however, it may be useful to additionally modify the processivity of these improved polymerases. For example, when performing polymerase chain reactions (PCR) for long templates, the use of highly processive polymerases often results in lower yields. Therefore, there is a need to modulate polymerase processivity to optimize the enzyme for specific purposes, e.g., long PCR.

Further, polymerase modification with a sequence-non-specific double-stranded nucleic acid binding domain may, in some cases, decrease polymerase discrimination between mismatched primer/templates and properly matched primer/template. Therefore, there can also be a need to increase the specificity of a polymerase for the primer template.

The current invention addresses both of these needs, i.e., the need for modulating processivity and primer/template binding specificity. The invention provides a polymerase conjugate comprising a mutated DNA binding domain such as Sso7d, Sac7d, or related domains joined to the polymerase or catalytic domain of the polymerase. The mutated binding domain comprises one or more amino acid substitutions at a face residue of the DNA binding domain polypeptide sequence. These substituted fusion polymerases exhibit enhanced performance capabilities in polymerase reactions, e.g., a polymerase chain reaction (PCR).

BRIEF SUMMARY OF THE INVENTION

This invention provides polymerase that have modulated processivity. In some embodiments, the polymerase also exhibits enhanced primer/template binding specificity. In particular, the invention provides an Sso7 polymerase conjugate protein comprising an Sso7 domain having at least 60% identity to SEQ ID NO:2 linked to a polymerase domain; wherein an amino acid at a position that is a face residue position as determined with reference to SEQ ID NO:2, is substituted with a different amino acid residue; wherein replacement of the face residue results in a processivity that is less than the processivity of a wildtype Sso7-polymerase fusion and greater than the processivity of the polymerase domain when it is not fused to an Sso7d domain. Often, replacement of the face residue also increases the polymerase primer/template binding specificity in comparison to an Sso7 polymerase fusion protein comprising SEQ ID NO:2.

In some embodiments, the face residue position is selected from the group consisting of a tryptophan residue at position 24, a valine residue at position 26, and a methionine residue at position 29. In particular embodiments, the face residue position is a tryptophan residue at position 24, and the replacement amino acid residue is any amino acid other than Asp, Glu, Arg, Lys, or Pro. Often, the replacement amino acid residue is glycine, valine, or alanine.

In preferred embodiments, the polymerase domain of the conjugates has thermally stable polymerase activity. The polymerase domain may be a family A polymerase domain, e.g., a *Thermus* polymerase domain or a family B polymerase domain, e.g., a *Pyrococcus* polymerase domain. Often, the polymerase domain is a ΔTaq polymerase domain.

In other embodiments, the Sso7 domain comprises SEQ ID NO:2 in which an amino acid at a position that is a face residue position is replace by a different amino acid. For example, in some embodiments, the Sso7 domain comprises SEQ ID NO:2 in which a tryptophan residue at position 24 is replaced with an amino acid residue selected from a group consisting of glycine, alanine, and valine.

In another aspect, the invention provides a method of performing a polymerase reaction on a target nucleic acid present in a solution, the method comprising: (a) contacting the target nucleic acid with a an Sso7 polymerase conjugate protein comprising an Sso7d domain having at least 60% identity to SEQ ID NO:2 linked to a polymerase domain; wherein an amino acid at a position that is a face residue position as determined with reference to SEQ ID NO:2, is replaced by an amino acid residue that does not occur at the face residue position in a wildtype Sso7 protein; and wherein replacement of the face residue results in a processivity that is greater than the processivity of the polymerase domain when it is not fused to an Sso7 domain; wherein the solution is of a composition that permits the binding domain to bind to the target nucleic acid and the polymerase domain to extend a primer that is hybridized to the target nucleic acid sequence; and (b) incubating the solution under conditions in which the primer is extended by the polymerase. Often, replacement of the face residue increases the polymerase primer/template binding specificity in comparison to an Sso7 polymerase fusion protein comprising SEQ ID NO:2.

The invention also provides methods of making and using the polymerase conjugates disclosed herein to modulate a polymerase reaction.

BRIEF DESCRIPTION OF THE DRAWINGS

FIG. 2 shows an alignment of Sac7e (SEQ ID NO:10) and Sso7d (SEQ ID NO:9). Consensus peptide=SEQ ID NOs:11-14.

DETAILED DESCRIPTION OF THE INVENTION

Definitions

Figure 1:
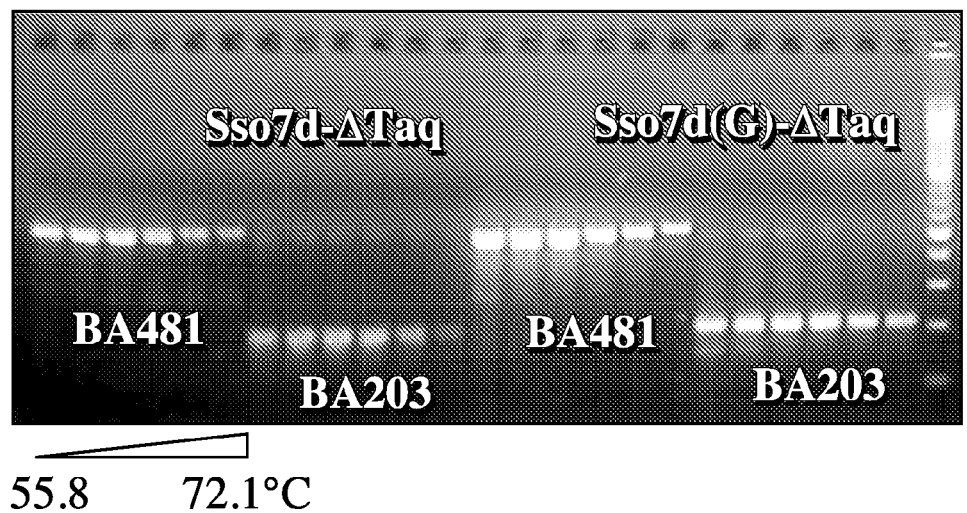
FIG. 1 depicts the results from a PCR reaction comparing Sso7d(G)-ΔTaq to the wildtype fusion protein, Sso7d-ΔTaq. The final PCR products were analyzed on a 1% agarose gel to assess the relative yields.

The term "Sso7" or "Sso7 DNA binding domain" or "Sso7-like DNA binding domain" refers to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 15, 25, 35, 50, or more amino acids, to the Sso7 sequence of SEQ ID NO:2; (2) bind to antibodies, e.g., polyclonal antibodies, raised against an immunogen comprising an amino acid sequence of SEQ ID NO:2 and conservatively modified variants thereof; (3) specifically hybridize under stringent hybridization conditions to an Sso7 nucleic acid sequence of SEQ ID NO:1 and conservatively modified variants thereof; (4) have a nucleic acid sequence that has greater than about 50%, preferably greater than about 60%, 65%, 70%, 75%, 80%, 85%, 90%, 95%, 96%, 97%, 98%, or 99% nucleotide sequence identity, preferably over a region of at least about 50, 100, 150, or more nucleotides, to SEQ ID NO:1; or (5) or are amplified by primers that specifically hybridize under stringent hybridization conditions to the same sequence as a primer set such as 5'-GCAACAG-TAAAGT TCAAGTACAAAGG-3' (SEQ ID NO:15) (forward) and 5'-CTAACATTTGTAGTAGTTCT TTTG-GAGCG-3', SEQ ID NO:16 (reverse). The term includes both full-length Sso7 polypeptides and fragments of the polypeptides that have sequence non-specific double-stranded DNA binding activity.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

The term "identical" in the context of two nucleic acids or polypeptide sequences refers to the residues in the two sequences that are the same when aligned for maximum correspondence, as measured using a "sequence comparison algorithms" described in the section below entitled "Identification of Sso7 domains based on homology".

A "wildtype Sso7" refers to a naturally occurring Sso7 protein. A "wildtype Sso7 amino acid sequence" refers to the naturally occurring amino acid sequence.

An "Sso7 polymerase conjugate" refers to a modified polymerase comprising at least one Sso7 DNA binding domain joined to a polymerase domain, or a catalytic subunit of the polymerase domain. A "substituted Sso7 polymerase conjugate" refers to a conjugate in which at least one face position amino acid residue is substituted with an amino acid residue that does not occur at that position in a native Sso7 sequence. An "Sso7 polymerase conjugate" may comprises multiple Sso7 binding domains.

"Efficiency" in the context of a nucleic acid modifying enzyme of this invention refers to the ability of the enzyme to perform its catalytic function under specific reaction conditions. Typically, "efficiency" as defined herein is indicated by the amount of product generated under given reaction conditions.

"Enhances" in the context of an enzyme refers to improving the activity of the enzyme, i.e., increasing the amount of product per unit enzyme per unit time.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

An amino acid residue "having a side chain volume that is less than the side chain volume of tryptophan refers to an amino acid residue with a side chain that is less bulky than tryptophan. Such a side chain typically has a volume of less than about 170 Å$^3$.

"Polymerase" refers to an enzyme that performs template-directed synthesis of polynucleotides. The term encompasses both the full length polypeptide or a domain that has polymerase activity.

"Processivity" refers to the ability of a polymerase to remain bound to the template or substrate and perform DNA synthesis. Processivity is measured by the number of catalytic events that take place per binding event.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus, Thermus brockianus*, and *Thermus thermophilus*; any recombinant enzymes deriving from *Thermus* species, and any functional derivatives thereof, whether derived by genetic modification or chemical modification or other methods known in the art.

The term "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

"Long PCR" refers to the amplification of a DNA fragment of 5 kb or longer in length. Long PCR is typically performed using specially-adapted polymerases or polymerase mixtures (see, e.g., U.S. Pat. Nos. 5,436,149 and 5,512,462) that are distinct from the polymerases conventionally used to amplify shorter products. 002310

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "temperature profile" refers to the temperature and lengths of time of the denaturation, annealing and/or extension steps of a PCR or cycle sequencing reaction. A temperature profile for a PCR or cycle sequencing reaction typically consists of 10 to 60 repetitions of similar or identical shorter temperature profiles; each of these shorter profiles may typically define a two step or three-step cycle. Selection of a temperature profile is based on various considerations known to those of skill in the art, see, e.g., Innis et al., supra. In a long PCR reaction as described herein, the extension time required to obtain an amplification product of 5 kb or greater in length is reduced compared to conventional polymerase mixtures.

PCR "sensitivity" refers to the ability to amplify a target nucleic acid that is present in low concentration. "Low concentration" refers to $10^4$, often $10^3$, $10^2$, $10^1$, or fewer, copies of the target sequence per microliter in the nucleic acid sample to be amplified.

The term "polymerase primer/template binding specificity" as used herein refers to the ability of an Sso7 fusion polymerase to discriminate between correctly matched primer/templates and mismatched primer templates. An "increase in polymerase primer/template binding specificity" in this context refers to an increased ability of an Sso7 variant fusion polymerases of the invention to discriminate between matched primer/template in comparison to a wildtype Sso7 polymerase fusion protein comprising SEQ ID NO:2, A "template" refers to a double stranded polynucleotide sequence that comprises the polynucleotide to be amplified, flanked by primer hybridization sites. Thus, a "target template" comprises the target polynucleotide sequence flanked by hybridization sites for a 5' primer and a 3' primer.

An "improved polymerase" includes a sequence-non-specific double-stranded DNA binding domain joined to the polymerase or polymerase domain. An "unimproved polymerase" or "unmodified polymerase" is a polymerase that does not have a sequence-non-specific double-stranded DNA binding domain.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Introduction

The current invention provides variant Sso7 polymerase conjugates that exhibit modulated processivity and/or an increased specificity relative to a wildtype Sso7 fusion polymerase. These polymerase reactions are often more efficient and yield more product compared to unmodified polymerases or wildtype Sso7 fusion polymerases. The variant fusion polymerases comprise a polymerase domain with an Sso7 binding domain joined to it. The Sso7 binding domain comprises an Sso7 in which amino acid residues at face positions are substituted to an amino acid that does not occur at that position in a known, wildtype Sso7.

Those of skill in the art will appreciate that substitutions to modulate processivity may be introduced into the nucleic acid binding domain of a polymerase comprising a heterologous sequence nonspecific double-stranded nucleic acid binding domain other than Sso7. For example, one or more substitutions may be introduced into particular positions (e.g., those that interact with DNA) of the DNA binding domain of a chimeric polymerase that has a sequence nonspecific helix-hairpin-helix (HhH) binding domain fused to the polymerase domain (e.g., Pavlov et al., *Proc. Natl. Acad. Sci.* USA 99:13510-13515, 2002).

Polymerases

DNA polymerases are well known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Similarly, RNA polymerases typically include eukaryotic RNA polymerases I, II, and III, and bacterial RNA polymerases as well as phage and viral polymerases. RNA polymerases can be DNA-dependent and RNA-dependent.

In specific embodiments, Taq polymerase domains are incorporated into the fusion protein. In particular polymerase variants such as ΔTaq, which is a genetically modified version of standard Taq DNA polymerase that lacks the 5' to 3'-exonuclease activity (Lawyer et al., *J Biol Chem* 264:6427-6437 (1989)), are often used in constructing the fusion polymerases of the invention. Other family A polymerases that act similarly to Taq, e.g., *Thermus brockianus* polymerase, which is about 90% similar to Taq polymerase, as well as *Thermus flavus* polymerase, and *Thermus thermophilus* polymerase, which has reverse transcriptase activity, may also be used. Additionally, less extremely thermophilic polymerases, such as the family A polymerase from *Bacillus stearothermophilus* are likely to prove useful, as are mesophilic polymerases such as *E. coli* Pol I and its deleted derivatives.

Family B polymerases such as *Pyrococcus* polymerases, e.g., Pfu polymerase, may also be used as a polymerase domain that is fused to a substituted Sso7 domain.

The activity of a polymerase can be measured using assays well known to those of skill in the art. For example, a processive enzymatic activity, such as a polymerase activity, can be measured by determining the amount of nucleic acid synthesized in a reaction, such as a polymerase chain reaction. In determining the relative efficiency of the enzyme, the amount of product obtained with a polymerase containing a sequence-non-specific double-stranded DNA binding domain can then be compared to the amount of product obtained with the normal polymerase enzyme, which will be described in more detail below and in the Examples.

A polymerase domain suitable for use in the invention can be the enzyme itself or the catalytic domain, e.g., Taq polymerase or a domain of Taq with polymerase activity. The catalytic domain may include additional amino acids and/or may be a variant that contains amino acid substitutions, deletions or additions, but still retains enzymatic activity.

Sso7 Proteins

The polymerases of the invention comprise an Sso7 polypeptide sequence that has amino acid substitutions at face residue positions. Sso7d is a small (63 amino acids, about 7,000 kd MW), basic chromosomal protein from the hyperthermophilic archaeabacteria *Sulfolobus solfataricus*. The protein is lysine-rich and has high thermal, acid and chemical stability. It binds to DNA in a sequence-independent manner and when bound, increase the $T_M$ of DNA by up to 40° C. under some conditions (McAfee et al., *Biochemistry* 34:10063-10077, 1995). Sso7d and its homologs are typically believed to be involved in packaging genomic DNA and stabilizing genomic DNA at elevated temperatures. The protein sequence is set forth in SEQ ID NO:2.

There are several known Sso7d-like proteins (also referred to as Sso7 proteins) including, but not limited to, Sac7a, Sac7b, Sac7d, and Sac7e, from the hyperthermophilic archaeabacteria *S. acidocaldarius*; and Ssh7a and Ssh7b, *Sulfolobus shibatae*. These proteins have an identity with Sso7d that ranges from 78% to 98%. Other Sso7 domains for use in the invention may also be identified as set forth below.

The face residue positions of an Sso7 protein are determined with reference to the Sso7d sequence as set forth in SEQ ID NO:2. Face residues are those residues that are exposed on the surface of the protein that interacts with the bases of a DNA double helix. These residue have been identified through structural studies of Sso7d (see, e.g, Gao et al., *Nature Struct. Biol.* 5:782-786, 1998). The surface face amino acids Trp24, Val26, Met29, Ser31, Arg43 and Ala45 of SEQ ID NO:2 are face residues that are typically substituted in the fusion polymerases of the invention. It should be understood that such position designations do not indicate the number of amino acids in the claimed molecule per se, but indicate where in the claimed molecule the residue occurs when the claimed molecule sequence is maximally aligned with SEQ ID NO:2. Alignment can be performed either manually or using a sequence comparison algorithm described below. For example, the substituted Sso7 protein at the N-terminus of the fusion polymerase sequence set forth in SEQ ID NO:4 has a glycine substituted for a naturally occurring tryptophan residue. This substitution occurs at the 29th amino acid residue of SEQ ID NO:4. However, with reference to SEQ ID NO:2, the substitution is at the Trp24 position. Based on alignments as described, the following residues are typically present at face positions in wildtype Sso7 proteins: 24-Trp; 26-Val; 29-Met; 31-Ser; 43-Arg; and 45-Ala.

An example of an alignment of an Sso7 protein, Sac7e, to SEQ ID NO:2 and the identification of the face residue positions is shown in FIG. 2. The alignment was obtained using the NCBI BLAST program with default parameters (see, e.g., Altschul et al., *Nucl. Acids Res.* 25:3389-3402, 1997). Sac7e has 78% identity to SEQ ID NO:2. In FIG. 2, the start methionine of Sso7d (see, SEQ ID NO:2) at position 1 is not shown. Thus, although the Ala residue is the first residue of the Sso7d sequence shown in FIG. 2, it corresponds to position 2 of SEQ ID NO:2. As noted above, the face residues of Sso7d are the Trp at position 24, the Val at position 26, the Met at position 29, the Ser at position 31, the Arg at position 43 and the Ala at position 45. The corresponding face residues of Sac7e are the Trp at position 24 when determined with reference to SEQ ID NO:2 (residue number 23 in the Sac7e sequence); the Val at position 26 (residue number 25 in the Sac 7e sequence); the Met at position 29 (residue number 28 of the Sac7e sequence); the Ser at position 31 (residue number 30 of the Sac7e sequence); the Arg at positions 43 (residue number 41 of the Sac7e sequence); and the Ala at position 45 (residue number 43 of the Sac7e sequence).

As the side chains of these residues interact directly with the bases in the minor groove, changing these residues to residues other than the wildtype amino acids can be used to modify the strength of the interaction with DNA, without destroying the structure of the Sso7 domain, reducing thermostability, or otherwise greatly reducing the ability of the domains to function in the current invention. Furthermore, a subset of the face residues, Trp24, Val26, Met 29, and Ala45, interact with a position where the DNA helix is kinked. Thus, mutation at one of these positions can be used to decrease the affinity of Sso7 domains for DNA containing a mismatch near the kinked position.

A face residue can be substituted with a variety of amino acid residues. Typically the substituted residue is one that does not occur in any other naturally occurring Sso7 protein at that position. Often, the substituted residue occupies less volume than the amino acid residue in the native sequence. For example, the side chain of tryptophan occupies the largest volume of the naturally occurring amino acids. Tryptophan can therefore be substituted with less bulky amino acids, in particular such residues as alanine, glycine, or valine, that occupy less space. Further, a residue that introduces a major structural change into the polypeptide, e.g., proline, or has the capacity to introduce such a change, e.g., cysteine, is typically avoided as a face residue substitution.

Charge and hydrophobicity may also be considered when substituting amino acids. The surface of Sso7d is highly basic, containing 2 arginines and 14 lysines. For example, it may be desirable to select an amino acid residue that has a neutral or weak positive charge. Changing any of the face amino acids to Glu or Asp, which are strongly acidic, is not expected to produce a functional protein.

Thus, face residues are typically substituted with Ala, Gly, H is, Iso, Leu, Met, Phe, Ser, Thr, Tyr, Asn, Gln, Cys, or Val. Further, the amino acid selected to be inserted into a fusion polypeptide of the invention to replace the desired face residue is frequently one that is not found in that face residue position in a naturally occurring Sso7 polypeptide.

Identification of Additional Sso7 Domains Based on Homology.

Other suitable Sso7 DNA binding domains for use in the invention can be identified based on their sequence homology to Sso7d. Typically, domains that have about 60% amino acid sequence identity, optionally about 70%, 75, 80, 85, 90, or 95-98% amino acid sequence identity to a known sequence non-specific double-stranded nucleic acid binding protein over a comparison window of about 30 amino acids, optionally about 50-70 amino acids, or the length of the entire protein, can be used in the invention. The sequence can be compared and aligned for maximum correspondence over a comparison window, or designated region as measured using one of the following sequence comparison algorithms or by manual alignment and visual inspection. For purposes of this patent, percent amino acid identity is determined by the default parameters of BLAST.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Identification of Sso7 Proteins Based on Cross-Reactive Binding to Sso7-Specific Antibodies Sso7 DNA binding proteins for use in the invention can also be identified by cross-reactivity using antibodies, preferably polyclonal antibodies, that bind to known Sso7 binding domains. Polyclonal antibodies are generated using methods well known to those of ordinary skill in the art (see, e.g., Coligan, *Current Protocols in Immunology* (1991); Harlow & Lane, *Antibodies, A Laboratory Manual* (1988)). Those proteins that are immunologically cross-reactive binding proteins can then be detected by a variety of assay methods. For descriptions of various formats and conditions that can be used, see, e.g., *Methods in Cell Biology: Antibodies in Cell Biology*, volume 37 (Asai, ed. 1993), Coligan, supra, and Harlow & Lane, supra.

Useful immunoassay formats include assays where a sample protein is immobilized to a solid support. For example, a cross-reactive binding protein can be identified using an immunoblot analysis such as a western blot. The western blot technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that bind to the sequence non-specific double-stranded nucleic acid binding domain. The antibodies specifically bind to cross-reactive polypeptides on the solid support. The antibodies may be directly labeled or alternatively may be subsequently detected using labeled antibodies (e.g., labeled sheep anti-mouse antibodies) that specifically bind to the anti-binding domain antibodies. Other immunoblot assays, such as analysis of recombinant protein libraries, are also useful for identifying proteins suitable for use in the invention.

Using this methodology under designated immunoassay conditions, immunologically cross-reactive proteins that bind to a particular antibody at least two times the background or more, typically more than 10 times background, and do not substantially bind in a significant amount to other proteins present in the sample can be identified.

Immunoassays in the competitive binding format can also be used for crossreactivity determinations. For example, polyclonal antisera are generated to a known, Sso7 domain, e.g., Sso7d. The target antigen can then be immobilized to a solid support. Non-target antigens having minor crossreactivity (if they exist) can be added to the assay to improve the selectivity of the sera. The ability of the added proteins to compete for binding of the antisera to the immobilized protein is compared to the ability of the Sso7 protein to compete with itself. The percent crossreactivity for the above proteins is calculated, using standard calculations. Those antisera with less than 10% crossreactivity with the added protein are selected and pooled. Cross-reacting antibodies to non-target antigens can also be removed from the pooled antisera by immunoabsorption with the non-target antigens. Antibodies that specifically bind to particular nucleic acid binding domains of the invention can also be made using this methodology.

The immunoabsorbed and pooled antisera are then used in a competitive binding immunoassay as described above to compare a second protein, thought to be perhaps an allele, polymorphic variant or a homolog of the known Sso7 binding domain, for example, a homolog from another species, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the nucleic acid binding domain protein that is required to inhibit 50% of binding, then the second protein is said to specifically bind to the polyclonal antibodies generated to the Sso7d immunogen.

The activity of the sequence non-specific double-stranded nucleic acid binding domains can be assessed using a variety of assays as described, e.g., in WO0192501. In the current invention, the Sso7 domain is substituted at least one face residue. The substituted Sso7 domains, when joined to a polymerase, exhibits modified processivity and/or an increase primer/template binding specificity. An Sso7 conjugate polymerase of the invention can be identified using assays well known in the art, which are further described herein.

Joining the Sso7 DNA Binding Domain to the Polymerase.

The Sso7 DNA binding domain and the polymerase domain, e.g., Sso7d and Taq polymerase, of the conjugate proteins of the invention can be joined by methods well known to those of skill in the art. These methods include both chemical and recombinant means.

Chemical means of joining the Sso7 protein to the polymerase are described, e.g., in *Bioconjugate Techniques*, Hermanson, Ed., Academic Press (1996). These include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The means of linking the Sso7 and polymerase domains of the conjugate protein may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) *J. Am. Chem. Soc.*, 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, *Proteins Structures and Molecular Principles*, 50-60 (1983)). The composition of the synthetic polypeptides or of subfragments of the polypeptide, may be confirmed by amino acid analysis or sequencing (e.g., the Edman degradation procedure; see Creighton, *Proteins, Structures and Molecular Principles*, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In another embodiment, the Sso7 and polymerase domains are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

In a specific embodiment, the coding sequences of each polypeptide in the fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) *Proc. Natl. Acad. Sci.* USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have nonessential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of joining the Sso7 and polymerase domains include ionic binding by expressing negative and positive tails and indirect binding through antibodies and streptavidin-biotin interactions. (See, e.g., *Bioconjugate Techniques*, supra). The domains may also be joined together through an intermediate interacting sequence. For example, an Sso7d-interacting sequence, i.e., a sequence that binds to Sso7d, can be joined to a polymerase. The resulting fusion protein can then be allowed to associate non-covalently with the Sso7d to generate an Sso7d-polymerase conjugate.

Production of Fusion Proteins Using Recombinant Techniques

In a typical embodiment, a conjugate Sso7-polymerase protein of the invention is produced by recombinant expression of a nucleic acid encoding the protein, which technique is standard practice in the art. Such a fusion product can be made by ligating the appropriate nucleic acid sequences encoding the desired amino acid sequences to each other by methods known in the art, in the proper coding frame, and expressing the product by methods known in the art.

Nucleic acids encoding the domains to be incorporated into the fusion proteins of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, *Gene Transfer and Expression: A Laboratory Manual* (1990); and *Current Protocols in Molecular Biology*(Ausubel et al., eds., 1994-1999).

Nucleic acid sequences that encode the Sso7 and polymerase polypeptides can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the Sso7 and polymerase sequences using a DNA or RNA template (see, e.g., Dieffenbach & Dveksler, PCR Primers: A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes.

In an example of obtaining a nucleic acid encoding an Sso7 or polymerase domain using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications*(Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomeli et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a polypeptide expressed from a particular nucleic acid can be compared to properties of an Sso7 polypeptide or polymerase to provide another method of identifying suitable nucleic acids.

One of skill will also recognize that modifications can additionally be made to the Sso7 and polymerase domains without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

One or more of the domains may also be modified to facilitate the linkage of the two domains to obtain the polynucleotides that encode the fusion polypeptides of the invention. Thus, Sso7 and polymerase domains that are modified by such methods are also part of the invention. For example, a codon for a cysteine residue can be placed at either end of a domain so that the domain can be linked by, for example, a sulfide linkage. The modification can be performed using either recombinant or chemical methods (see, e.g., Pierce Chemical Co. catalog, Rockford Ill.).

The Sso7 and polymerase domains of the recombinant fusion protein are often joined by linker domains, usually polypeptide sequences including Gly, Ser, Ala, and Val such as those described above. In some embodiments, proline residues are incorporated into the linker to prevent the formation of significant secondary structural elements by the linker.

In some embodiments, the recombinant nucleic acids the recombinant nucleic acids encoding the proteins of the invention are modified to provide preferred codons which enhance translation of the nucleic acid in a selected organism (e.g., yeast preferred codons are substituted into a coding nucleic acid for expression in yeast).

Expression Cassettes and Host Cells for Expressing the Fusion Polypeptides

There are many expression systems for producing the fusion polypeptides that are well know to those of ordinary skill in the art. (See, e.g., *Gene Expression Systems*, Fernandex and Hoeffler, Eds. Academic Press, 1999; Sambrook $ Russell, supra; and Ausubel et al, supra.) Typically, the polynucleotide that encodes the fusion polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, and fusion expression systems such as GST and LacZ. Epitope tags can also be added to recombinant proteins to provide convenient methods of isolation, e.g., c-myc, HA-tag, 6-His (SEQ ID NO:17) tag, maltose binding protein, VSV-G tag, anti-DYKDDDDK (SEQ ID NO:18) tag, or any such tag, a large number of which are well known to those of skill in the art.

For expression of fusion polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983)*Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J.K. Setlow, Ed., Plenum Press, NY; commercially available from Qiagen (Santa Clarita, Calif.)).

Introduction of Mutations into Sso7 Sequences

The Sso7 sequences of the invention contain substitutions at face residues. One of skill will recognize that there are many ways of generating these alterations or variants of a given nucleic acid sequence. Such well-known methods include site-directed mutagenesis, PCR amplification using degenerate oligonucleotides, chemical synthesis of a desired oligonucleotide (e.g., in conjunction with ligation and/or cloning to generate large nucleic acids) and other well-known techniques. See, Giliman & Smith, Gene 8:81-97 (1979), Roberts, et al., Nature 328:731-734 (1987) and Sambrook, Innis, and Ausubel (all supra).

In one example of generating an Sso7 sequence of the invention, site directed mutagenesis is used to substitute an amino acid residue for the face residue. The nucleic acid sequence is substituting by synthesizing an oligonucleotide primer that contains the mutation. The primer is hybridized to an Sso7 nucleic acid, e.g., SEQ ID NO:1, and a new sequence amplified. The amplification product with the mutation may then ligated into an expression vector.

Most commonly, polypeptide sequences are altered as above, i.e., by changing the corresponding nucleic acid sequence and expressing the polypeptide. However, polypeptide sequences can also be generated synthetically using commercially available peptide synthesizers to produce a desired polypeptide (see, Merrifield, and Stewart & Young, supra).

Finally, the substituted Sso7 sequences are evaluated by using techniques such as those described below to identify the fusion polymerases that exhibit increased primer/template recognition specificity and/or a processivity that is increased relative to an unmodified polymerase. Typically the processivity of a substituted fusion protein is less than that of a wildtype Sso7 fusion polymerase.

Modulation of Polymerase Activity

The fusion polymerases of the invention exhibit modulated activity that includes both increased processivity relative to an unmodified polymerase and improved primer/template binding specificity. The activities can be measured using techniques that are standard in the art.

A fusion polymerase of the invention often exhibits an increase in primer/template specificity in comparison to a fusion polymerase comprising a wildtype Sso7 sequence, e.g., SEQ ID NO:2. Primer/template specificity is the ability of an enzyme to discriminate between matched primer/template duplexes and mismatched primer/template duplexes. Specificity can be determined, for example, by comparing the relative yield of two reactions, one of which employs a matched primer, and one of which employs a mismatched primer. An enzyme with increased discrimination will have a higher relative yield with the matched primer than with the mismatched primer, i.e., the ratio of the yield in the reaction using the matched primer vs. the reaction using the mismatched primer is about 1 or above. This ratio can then be compared to the yield obtained in a parallel set of reactions employing a fusion polymerase comprising the wildtype Sso7 domain. A fusion protein of the invention typically exhibits at least a 2-fold, often 3-fold or greater increase in the ratio relative to a wildtype fusion polymerase.

Specificity can also be measured, e.g., in a real-time PCR, where the difference in the Ct (threshold cycle) values ($\Delta C_t$) between the fully complementary primer/template and the mismatched primer/template can be used to measure primer/template binding specificity of different enzymes. The Ct value represents the number of cycles required to generate a detectable amount of DNA (a "detectable" amount of DNA is typically 2×, usually 5×, 10×, 100× or more above background). A polymerase with enhanced specificity may be able to produce a detectable amount of DNA in a smaller number of cycles by more closely approaching the theoretical maximum amplification efficiency of PCR. Accordingly, a lower Ct value reflects a greater amplification efficiency for the enzyme.

Polymerase processivity can be measured by a variety of methods known to those of ordinary skill in the art. Polymerase processivity is generally defined as the number of nucleotides incorporated during a single binding event of a modifying enzyme to a primed template. For example, a 5' FAM-labeled primer is annealed to circular or linearized ssM13mp18 DNA to form a primed template. In measuring processivity, the primed template usually is present in significant molar excess to the polymerase so that the chance of any primed template being extended more than once by the polymerase is minimized. The primed template is therefore mixed with the polymerase at a ratio such as approximately 4000:1 (primed DNA:DNA polymerase) in the presence of buffer and dNTPs. $MgCl_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a protein of the invention, i.e., a substituted fusion polymerases that contains a substituted Sso7 nucleic acid binding domain fused to the catalytic domain of a polymerase, is then compared to the processivity of the enzyme without the binding domain (an unmodified polymerase) and the processivity of a fusion polymerase comprising a wildtype Sso7 sequence. The substituted fusion polymerase of the invention exhibits increased processivity relative to the unmodified polymerase and typically, decreased processivity relative to the wildtype Sso7 fusion polymerase.

Enhanced efficiency can also be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12 nucleotide in length, primer annealed at an elevated temperature, e.g., 50° C. In this analysis, enhanced efficiency is shown by the ability of a polymerase to produce more product in a PCR reaction using the 12 nucleotide primer annealed at 50° C. when it is joined to a substituted Sso7d sequence in comparison to an unmodified polymerase.

Long PCR may be used as another of demonstrating enhanced efficiency. For example, an enzyme with enhanced efficiency typically allows the amplification of a long amplicon (>5 kb) in a shorter extension time compared to an enzyme with relatively lower efficiency.

Assays such as salt sensitivity can also be used to demonstrate improvement in efficiency of a processive nucleic acid modifying enzyme of the invention. A polymerase, when fused to an Sso7 sequence of the invention exhibits increased tolerance to high salt concentrations, i.e., a processive enzyme with increased processivity can produce more product in higher salt concentrations. For example, a PCR analysis can be performed to determine the amount of product obtained in a reaction using a substituted Sso7 fusion Taq polymerase compared to an unmodified Taq polymerase in reaction conditions with high salt, e.g., 80 mM.

Other methods of assessing enhanced efficiency of the improved polymerases of the invention can be determined by those of ordinary skill in the art using standard assays of the enzymatic activity of a given modification enzyme.

EXAMPLES

Example 1

Construction of Mutant Sso7-ΔTaq Fusions

Sequential PCR was used to introduce the point mutations at the codon encoding W24 in the wild type Sso7d-ΔTaq set forth in SEQ ID NO:2. In the first round of PCR, primer pair M13R (5'-GCGGATAACAATTTCACACAGG-3'; SEQ ID NO:19) and W24T (5'-ATCTCCAAGATCAA GAAAG-TAGNGCGTGTGGGCAAGATG-3'; SEQ ID NO:20), and primer pair W24AEVG-B (5'-CTACTTTCTTGATCTTG-GAGAT-3'; SEQ ID NO:21) and 1008R (5'-GAGGGCTT-TATAAGGCTCG-3'; SEQ ID NO:22) were used to amplify the corresponding regions from pYW1 (see, PCT publication WO 01/92501). The products from the first PCR were purified and combined together with primers M13R and 1008R in a second round of PCR to produce a 400 bp fragment. This fragment was digested with restriction enzymes EcoRI and BstXI and inserted into the corresponding site of pYW1. Primer W24-T contains a degenerate nucleotide at position 23 from the 5' end, so that the final oligonucleotide will be a mixed population containing 25% each of G, T, A, and C at this position. As the result, the codon GNG encodes one of the following four amino acids, Gly (GGG) (SEQ ID NO:3, bolded and underlined); Val (GTG) (SEQ ID NO:5, bolded and underlined); Glu (GAG) (SEQ ID NO:7, bolded and under); or Ala (GCG) in the mutant fusion protein.

Example 2

Mismatch Primer Assay

Based on structural studies (Gao et al., *Nature Struct. Biol.* 5:782-786, 1998), the W24 residue in wildtype Sso7d is involved in anchoring a base in its unstacked position. This example shows that mutation at this position results in an increase in the primer-template binding specificity of the fusion protein.

Two pairs of primers were used to assess the ability of a PCR enzyme in discriminating matched primers and mismatched primers. The matched primer, 57F (5'-TCCGTTCT-TCTTCGTCATAACT-3'; SEQ ID NO:23), is fully complementary to lambda DNA. The mismatched primer, 57F5/6 (5'-TCCGCCCTTCTTCGTCATAACT-3'; SEQ ID NO:24), contains two bases (position 5 and 6 from the 5' end) that are not complementary to lambda DNA template. The same matched reverse primer, 732R (5'-CCTGACTGTTC- GATATATTCACTC-3'; SEQ ID NO:25), is used with 57F or 57F5/6 to produce a 675 bp amplicon. The cycling program used was: 94° C.-1 min, 20×(94° C.-10 s, 50-74° C.-30 s, 72° C.-1 min), 72° C.-10 min. The final yield of the PCR products was quantified using a PicoGreen dilution in TE buffer (1:200 PicoGreen:TE) and a fluorescent plate reader. For each enzyme, two PCR amplifications were performed, one using primers 57F and 732R, and the other using primers 57F5/6 and 732R.

The ability of an enzyme to discriminate mismatched and matched primers was determined by comparing the relative yield of the two reactions. The more discriminative enzyme should have a higher relative yield with the matched primer than with the mismatched primer. Table 1 shows the results analyzed at annealing temperature of 64° C. The wild type fusion protein was the least discriminative of matched and mismatched primers. The three mutant proteins showed 2.5-14-fold improvement over the wild type fusion protein.

TABLE 1

Compare match and mismatch discrimination in PCR

| Enzymes | Ratio of yield (Match/mismatch) | Relative to Sso7d-ΔTaq |
|---|---|---|
| Taq | 7.7 | 8.4 x |
| Sso7d-ΔTaq | 0.92 | 1 x |
| Sso7d(G)-ΔTaq | 3.3 | 3.6 x |
| Sso7d(V)-ΔTaq | 2.3 | 2.5 x |
| Sso7d(E)-ΔTaq | 12.8 | 14 x |

Example 3

Processivity Comparison of Wild-Type and Mutant Fusion Proteins

As the binding interaction between Sso7d and dsDNA is important to the enhancement of processivity of the fusion protein, the mutations introduced may abolish the enhancement. The processivity assay (see, PCT publication WO 01/92501) was used to measure the processivity of fusion proteins containing mutations at residue W24 of Sso7d, and the results are summarized in Table 2. Two of the three mutant proteins, W24G and W24V, still maintained a 2-fold higher processivity than the unmodified protein, ΔTaq. The mutant protein containing the W24E change exhibits the same processivity as the unmodified protein. These results suggest that different mutations at this position could have differential effect on the processivity of the fusion protein.

TABLE 2

Processivity comparison

| Enzymes | Processivity (in Median product length) |
|---|---|
| ΔTaq | 4-6 nt |
| Taq | 13-18 nt |
| Sso7d-ΔTaq | 31-39 nt |
| Sso7d(G)-ΔTaq | 8-10 nt |
| Sso7d(V)-ΔTaq | 7-11 nt |
| Sso7d(E)-ΔTaq | 4-6 nt |

Example 4

Mutant Proteins are More Efficient in Late Cycles of PCR Amplification

The mutant proteins were compared with the wildtype protein in PCR applications. Two criteria were used in the comparison, one was the threshold cycle (Ct) value in qPCR applications, which reflects the efficiency of the enzyme in early cycles of amplification, and the other was the final yield of the PCR product, which reflects the efficiency of the enzyme in late cycles of amplification. SYBR green-based qPCR reactions were used to amplify two beta-actin amplicons, BA481 and BA203, from human genomic DNA. The reactions contained a final concentration of 1×SYBR Green I and 2 mM $MgCl_2$. An annealing gradient of 55.8° C. to 72.1° C. was used. The Ct values are summarized in Table 3. Very similar Ct values (<1 cycle difference) were obtained for the wildtype fusion protein and the Sso7d(G) fusion protein, suggesting that there is no significant difference in efficiency between the two enzymes in the early cycles.

The final PCR products were analyzed on 1% agarose gel to assess the relative yields. As shown in FIG. 1, the final yields of both BA481 and BA203 amplicons were significantly higher when the mutant protein, Sso(G)-ΔTaq, was used than when the wildtype fusion protein was used, which is consistent with the mutant protein being more efficient in the late cycles of amplification.

TABLE 3

Comparison of Ct values at 66° C. annealing temperature

| Enzyme (10 U/ml) | BA481 | BA203 |
|---|---|---|
| Sso7d-ΔTaq | 25 | 24.2 |
| Sso7d(G)-ΔTaq | 25.8 | 23.7 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
Table of Sso7d and Sso7d fusion sequences

SEQ ID NO: 1
ATGGCAACCGTAAAGTTCAAGTACAAAGGCGAAGAAAAAGAGGTAGACAT
CTCCAAGATCAAGAAAGTATGGCGTGTGGGCAAGATGATCTCCTTCACCT
ACGACGAGGGCGGTGGCAAGACCGGCCGTGGTGCGGTAAGCGAAAAGGAC
GCGCCGAAGGAGCTGCTGCAGATGCTGGAGAAGCAGAAAAAG

SEQ ID NO: 2
MATVKFKYKGEEKEVDISKIKKVWRVGKMISFTYDEGGGKTGRGAVSEKD
APKELLQMLEKQKK

SEQ ID NO: 3
DNA sequence encoding Sso7d(G)-ΔTaq
ATGATTACGAATTCGAGCGCAACCGTAAAGTTCAAGTACAAAGGCGAAGA
AAAAGAGGTAGACATCTCCAAGATCAAGAAAGTAGGGCGTGTGGGCAAGA
TGATCTCCTTCACCTACGACGAGGGCGGTGGCAAGACCGGCCGTGGTGCG
GTAAGCGAAAAGGACGCGCCGAAGGAGCTGCTGCAGATGCTGGAGAAGCA
GAAAAAGGGCGGCGGTGTCACTAGTCCCAAGGCCCTGGAGGAGGCCCCCT
GGCCCCGCCGGAAGGGGCCTTCGTGGGCTTTGTGCTTTCCCGCAAGGAG
CCCATGTGGGCCGATCTTCTGGCCCTGGCCGCCGCCAGGGGGGGCCGGGT
CCACCGGGCCCCGAGCCTTATAAAGCCCTCAGGGACCTGAAGGAGGCGC
GGGGGCTTCTCGCCAAAGACCTGAGCGTTCTGGCCCTGAGGGAAGGCCTT
GGCCTCCCGCCCGGCGACGACCCCATGCTCCTCGCCTACCTCCTGGACCC
TTCCAACACCACCCCCGAGGGGGTGGCCCGGCGCTACGCGGGGAGTGGA
CGGAGGAGGCGGGGAGCGGGCCGCCCTTTCCGAGAGGCTCTTCGCCAAC
CTGTGGGGAGGCTTGAGGGGAGAGAGGCTCCTTTGGCTTTACCGGA
GGTGGAGAGGCCCCTTTCCGCTGTCCTGGCCCACATGGAGGCCACGGGG
TGCGCCTGGACGTGGCCTATCTCAGGGCCTTGTCCCTGGAGGTGGCCGAG
GAGATCGCCCGCCTCGAGGCCGAGGTCTTCCGCCTGGCCGGCCACCCCTT
CAACCTCAACTCCCGGGACCAGCTGGAAAGGGTCCTCTTTGACGAGCTAG
```

Table of Sso7d and Sso7d fusion sequences

```
GGCTTCCCGCCATCGGCAAGACGGAGAAGACCGGCAAGCGCTCCACCAGC
GCCGCCGTCCTGGAGGCCCTCCGCGAGGCCCACCCCATCGTGGAGAAGAT
CCTGCAGTACCGGGAGCTCACCAAGCTGAAGAGCACCTACATTGACCCCT
TGCCGGACCTCATCCACCCCAGGACGGGCCGCCTCCACACCCGCTTCAAC
CAGACGGCCACGGCCACGGGCAGGCTAAGTAGCTCCGATCCCAACCTCCA
GAACATCCCCGTCCGCACCCCGCTTGGGCAGAGGATCCGCCGGGCCTTCA
TCGCCGAGGAGGGGTGGCTATTGGTGGCCCTGGACTATAGCCAGATAGAG
CTCAGGGTGCTGGCCCACCTCTCCGGCGACGAGAACCTGATCCGGGTCTT
CCAGGAGGGGCGGGACATCCACACGGAGACCGCCAGCTGGATGTTCGGCG
TCCCCGGGAGGCCGTGGACCCCCTGATGCGCCGGGCGGCCAAGACCATC
AACTTCGGGGTCCTCTACGGCATGTCGGCCCACCGCCTCTCCCAGGAGCT
AGCCATCCCTTACGAGGAGGCCCAGGCCTTCATTGAGCGCTACTTTCAGA
GCTTCCCCAAGGTGCGGGCCTGGATTGAGAAGACCCTGGAGGAGGGCAGG
AGGCGGGGGTACGTGGAGACCCTCTTCGGCCGCCGCCGCTACGTGCCAGA
CCTAGAGGCCCGGGTGAAGAGCGTGCGGGAGGCGGCCGAGCGCATGGCCT
TCAACATGCCCGTCCAGGGCACCGCCGCCGACCTCATGAAGCTGGCTATG
GTGAAGCTCTTCCCCAGGCTGGAGGAAATGGGGGCCAGGATGCTCCTTCA
GGTCCACGACGAGCTGGTCCTCGAGGCCCCAAAAGAGAGGGCGGAGGCCG
TGGCCCGGCTGGCCAAGGAGGTCATGGAGGGGGTGTATCCCCTGGCCGTG
CCCCTGGAGGTGGAGGTGGGGATAGGGGAGGACTGGCTCTCCGCCAAGGA
GGGCATTGATGGCCGCGGCGGAGGCGGGCATCATCATCATCATCATTAAT
GAGATCT
```

SEQ ID NO: 4

Amino acid sequence of fusion protein Sso7d(G)-ΔTaq

The bolded, underlined residue indicates the amino acid substitution relative to wildtype Sso7d-ΔTaq.

```
MITNSSATVKFKYKGEEKEVDISKIKKVGRVGKMISFTYDEGGGKTGRGA
VSEKDAPKELLQMLEKQKKGGGVTSPKALEEAPWPPPEGAFVGFVLSRKE
PMWADLLALAAARGGRVHRAPEPYKALRDLKEARGLLAKDLSVLALREGL
GLPPGDDPMLLAYLLDPSNTTPEGVARRYGGEWTEEAGERAALSERLFAN
LWGRLEGEERLLWLYREVERPLSAVLAHMEATGVRLDVAYLRALSLEVAE
EIARLEAEVFRLAGHPFNLNSRDQLERVLFDELGLPAIGKTEKTGKRSTS
AAVLEALREAHPIVEKILQYRELTKLKSTYIDPLPDLIHPRTGRLHTRFN
QTATATGRLSSSDPNLQNIPVRTPLGQRIRRAFIAEEGWLLVALDYSQIE
LRVLAHLSGDENLIRVFQEGRDIHTETASWMFGVPREAVDPLMRRAAKTI
NFGVLYGMSAHRLSQELAIPYEEAQAFIERYFQSFPKVRAWIEKTLEEGR
RRGYVETLFGRRRYVPDLEARVKSVREAAERMAFNMPVQGTAADLMKLAM
VKLFPRLEEMGARMLLQVHDELVLEAPKERAEAVARLAKEVMEGVYPLAV
PLEVEVGIGEDWLSAKEGIDGRGGGHHHHHH
```

SEQ ID NO: 5

DNA sequence encoding Sso7d(V)-ΔTaq

```
ATGATTACGAATTCGAGCGCAACCGTAAAGTTCAAGTACAAAGGCGAAGA
AAAAGAGGTAGACATCTCCAAGATCAAGAAAGTAGTGCGTGTGGGCAAGA
TGATCTCCTTCACCTACGACGAGGGCGGTGGCAAGACCGGCCGTGGTGCG
GTAAGCGAAAAGGACGCGCCGAAGGAGCTGCTGCAGATGCTGGAGAAGCA
GAAAAAGGGCGGCGGTGTCACTAGTCCCAAGGCCCTGGAGGAGGCCCCCT
GGCCCCCGCCGGAAGGGGCCTTCGTGGGCTTTGTGCTTTCCCGCAAGGAG
CCCATGTGGGCCGATCTTCTGGCCCTGGCCGCCGCCAGGGGGGGCCGGGT
CCACCGGGCCCCGAGCCTTATAAAGCCCTCAGGGACCTGAAGGAGGCGC
GGGGGCTTCTCGCCAAAGACCTGAGCGTTCTGGCCCTGAGGGAAGGCCTT
GGCCTCCCGCCCGGCGACGACCCCATGCTCCTCGCCTACCTCCTGGACCC
TTCCAACACCACCCCCGAGGGGGTGGCCCGGCGCTACGGCGGGGAGTGGA
CGGAGGAGGCGGGGGAGCGGGCCGCCCTTTCCGAGAGGCTCTTCGCCAAC
CTGTGGGGAGGCTTGAGGGGGAGGAGAGGCTCCTTTGGCTTTACCGGGA
GGTGGAGAGGCCCCTTTCCGCTGTCCTGGCCCACATGGAGGCCACGGGG
TGCGCCTGGACGTGGCCTATCTCAGGGCCTTGTCCCTGGAGGTGGCCGAG
GAGATCGCCCGCCTCGAGGCCGAGGTCTTCCGCCTGGCCGGCCACCCCTT
CAACCTCAACTCCCGGGACCAGCTGGAAAGGGTCCTCTTTGACGAGCTAG
GGCTTCCCGCCATCGGCAAGACGGAGAAGACCGGCAAGCGCTCCACCAGC
GCCGCCGTCCTGGAGGCCCTCCGCGAGGCCCACCCCATCGTGGAGAAGAT
CCTGCAGTACCGGGAGCTCACCAAGCTGAAGAGCACCTACATTGACCCCT
TGCCGGACCTCATCCACCCCAGGACGGGCCGCCTCCACACCCGCTTCAAC
CAGACGGCCACGGCCACGGGCAGGCTAAGTAGCTCCGATCCCAACCTCCA
GAACATCCCCGTCCGCACCCCGCTTGGGCAGAGGATCCGCCGGGCCTTCA
TCGCCGAGGAGGGGTGGCTATTGGTGGCCCTGGACTATAGCCAGATAGAG
CTCAGGGTGCTGGCCCACCTCTCCGGCGACGAGAACCTGATCCGGGTCTT
CCAGGAGGGGCGGGACATCCACACGGAGACCGCCAGCTGGATGTTCGGCG
TCCCCGGGAGGCCGTGGACCCCCTGATGCGCCGGGCGGCCAAGACCATC
AACTTCGGGGTCCTCTACGGCATGTCGGCCCACCGCCTCTCCCAGGAGCT
AGCCATCCCTTACGAGGAGGCCCAGGCCTTCATTGAGCGCTACTTTCAGA
GCTTCCCCAAGGTGCGGGCCTGGATTGAGAAGACCCTGGAGGAGGGCAGG
AGGCGGGGGTACGTGGAGACCCTCTTCGGCCGCCGCCGCTACGTGCCAGA
CCTAGAGGCCCGGGTGAAGAGCGTGCGGGAGGCGGCCGAGCGCATGGCCT
TCAACATGCCCGTCCAGGGCACCGCCGCCGACCTCATGAAGCTGGCTATG
GTGAAGCTCTTCCCCAGGCTGGAGGAAATGGGGGCCAGGATGCTCCTTCA
```

Table of Sso7d and Sso7d fusion sequences

```
GGTCCACGACGAGCTGGTCCTCGAGGCCCCAAAAGAGAGGGCGGAGGCCG
TGGCCCGGCTGGCCAAGGAGGTCATGGAGGGGGTGTATCCCCTGGCCGTG
CCCCTGGAGGTGGAGGTGGGGATAGGGGAGGACTGGCTCTCCGCCAAGGA
GGGCATTGATGGCCGCGGCGGAGGCGGGCATCATCATCATCATCATTAAT
GAGATCT
```

SEQ ID NO: 6

Amino acid sequence of fusion protein Sso7d(V)-ΔTaq

The bolded, underlined residue indicates the amino acid substitution relative to wildtype Sso7d-ΔTaq.

```
MITNSSATVKFKYKGEEKEVDISKIKKVVRVGKMISFTYDEGGGKTGRGA
VSEKDAPKELLQMLEKQKKGGGVTSPKALEEAPWPPPEGAFVGFVLSRKE
PMWADLLALAAARGGRVHRAPEPYKALRDLKEARGLLAKDLSVLALREGL
GLPPGDDPMLLAYLLDPSNTTPEGVARRYGGEWTEEAGERAALSERLFAN
LWGRLEGEERLLWLYREVERPLSAVLAHMEATGVRLDVAYLRALSLEVAE
EIARLEAEVFRLAGHPFNLNSRDQLERVLFDELGLPAIGKTEKTGKRSTS
AAVLEALREAHPIVEKILQYRELTKLKSTYIDPLPDLIHPRTGRLHTRFN
QTATATGRLSSSDPNLQNIPVRTPLGQRIRRAFIAEEGWLLVALDYSQIE
LRVLAHLSGDENLIRVFQEGRDIHTETASWMFGVPREAVDPLMRRAAKTI
NFGVLYGMSAHRLSQELAIPYEEAQAFIERYFQSFPKVRAWIEKTLEEGR
RRGYVETLFGRRRYVPDLEARVKSVREAAERMAFNMPVQGTAADLMKLAM
VKLFPRLEEMGARMLLQVHDELVLEAPKERAEAVARLAKEVMEGVYPLAV
PLEVEVGIGEDWLSAKEGIDGRGGGGHHHHHH
```

SEQ ID NO: 7

DNA sequence encoding Sso7d(E)-ΔTaq

```
ATGATTACGAATTCGAGCGCAACCGTAAAGTTCAAGTACAAAGGCGAAGA
AAAAGAGGTAGACATCTCCAAGATCAAGAAAGTAGAGCGTGTGGGCAAGA
TGATCTCCTTCACCTACGACGAGGGCGGTGGCAAGACCGGCCGTGGTGCG
GTAAGCGAAAAGGACGCGCCGAAGGAGCTGCTGCAGATGCTGGAGAAGCA
GAAAAAGGGCGGCGGTGTCACTAGTCCCAAGGCCCTGGAGGAGGCCCCCT
GGCCCCCGCCGGAAGGGGCCTTCGTGGGCTTTGTGCTTTCCCGCAAGGAG
CCCATGTGGGCCGATCTTCTGGCCCTGGCCGCCGCCAGGGGGGGCCGGGT
CCACCGGGCCCCGAGCCTTATAAAGCCCTCAGGGACCTGAAGGAGGCGC
GGGGGCTTCTCGCCAAAGACCTGAGCGTTCTGGCCCTGAGGGAAGGCCTT
GGCCTCCCGCCCGGCGACGACCCCATGCTCCTCGCCTACCTCCTGGACCC
TTCCAACACCACCCCCGAGGGGGTGGCCCGGCGCTACGGCGGGGAGTGGA
CGGAGGAGGCGGGGGAGCGGGCCGCCCTTTCCGAGAGGCTCTTCGCCAAC
CTGTGGGGAGGCTTGAGGGGGAGGAGAGGCTCCTTTGGCTTTACCGGGA
GGTGGAGAGGCCCCTTTCCGCTGTCCTGGCCCACATGGAGGCCACGGGG
TGCGCCTGGACGTGGCCTATCTCAGGGCCTTGTCCCTGGAGGTGGCCGAG
GAGATCGCCCGCCTCGAGGCCGAGGTCTTCCGCCTGGCCGGCCACCCCTT
CAACCTCAACTCCCGGGACCAGCTGGAAAGGGTCCTCTTTGACGAGCTAG
GGCTTCCCGCCATCGGCAAGACGGAGAAGACCGGCAAGCGCTCCACCAGC
GCCGCCGTCCTGGAGGCCCTCCGCGAGGCCCACCCCATCGTGGAGAAGAT
CCTGCAGTACCGGGAGCTCACCAAGCTGAAGAGCACCTACATTGACCCCT
TGCCGGACCTCATCCACCCCAGGACGGGCCGCCTCCACACCCGCTTCAAC
CAGACGGCCACGGCCACGGGCAGGCTAAGTAGCTCCGATCCCAACCTCCA
GAACATCCCCGTCCGCACCCCGCTTGGGCAGAGGATCCGCCGGGCCTTCA
TCGCCGAGGAGGGGTGGCTATTGGTGGCCCTGGACTATAGCCAGATAGAG
CTCAGGGTGCTGGCCCACCTCTCCGGCGACGAGAACCTGATCCGGGTCTT
CCAGGAGGGGCGTGGACCCCCTGATGCGCCGGGCGGCCAAGACCATC
AACTTCGGGGTCCTCTACGGCATGTCGGCCCACCGCCTCTCCCAGGAGCT
AGCCATCCCTTACGAGGAGGCCCAGGCCTTCATTGAGCGCTACTTTCAGA
GCTTCCCCAAGGTGCGGGCCTGGATTGAGAAGACCCTGGAGGAGGGCAGG
AGGCGGGGGTACGTGGAGACCCTCTTCGGCCGCCGCCGCTACGTGCCAGA
CCTAGAGGCCCGGGTGAAGAGCGTGCGGGAGGCGGCCGAGCGCATGGCCT
TCAACATGCCCGTCCAGGGCACCGCCGCCGACCTCATGAAGCTGGCTATG
GTGAAGCTCTTCCCCAGGCTGGAGGAAATGGGGGCCAGGATGCTCCTTCA
GGTCCACGACGAGCTGGTCCTCGAGGCCCCAAAAGAGAGGGCGGAGGCCG
TGGCCCGGCTGGCCAAGGAGGTCATGGAGGGGGTGTATCCCCTGGCCGTG
CCCCTGGAGGTGGAGGTGGGGATAGGGGAGGACTGGCTCTCCGCCAAGGA
GGGCATTGATGGCCGCGGCGGAGGCGGGCATCATCATCATCATCATTAAT
GAGATCT
```

SEQ ID NO: 8

Amino acid sequence of fusion protein Sso7d(E)-ΔTaq

The bolded, underlined residue indicates the amino acid substitution relative to wildtype Sso7d-ΔTaq.

```
MITNSSATVKFKYKGEEKEVDISKIKKVERVGKMISFTYDEGGGKTGRGA
VSEKDAPKELLQMLEKQKKGGGVTSPKALEEAPWPPPEGAFVGFVLSRKE
PMWADLLALAAARGGRVHRAPEPYKALRDLKEARGLLAKDLSVLALREGL
GLPPGDDPMLLAYLLDPSNTTPEGVARRYGGEWTEEAGERAALSERLFAN
LWGRLEGEERLLWLYREVERPLSAVLAHMEATGVRLDVAYLRALSLEVAE
EIARLEAEVFRLAGHPFNLNSRDQLERVLFDELGLPAIGKTEKTGKRSTS
```

| Table of Sso7d and Sso7d fusion sequences |
|---|
| AAVLEALREAHPIVEKILQYRELTKLKSTYIDPLPDLIHPRTGRLHTRFN |
| QTATATGRLSSSDPNLQNIPVRTPLGQRIRRAFIAEEGWLLVALDYSQIE |
| LRVLAHLSGDENLIRVFQEGRDIHTETASWMFGVPREAVDPLMRRAAKTI |
| NFGVLYGMSAHRLSQELAIPYEEAQAFIERYFQSFPKVRAWIEKTLEEGR |

| Table of Sso7d and Sso7d fusion sequences |
|---|
| RRGYVETLFGRRRYVPDLEARVKSVREAAERMAFNMPVQGTAADLMKLAM |
| VKLFPRLEEMGARMLLQVHDELVLEAPKERAEAVARLAKEVMEGVYPLAV |
| PLEVEVGIGEDWLSAKEGIDRGRGGGGHHHHHH |

What is claimed is:

1. An Sso7 polymerase conjugate protein having template-dependent polynucleotide synthesis activity comprising an Sso7 domain linked to a polymerase domain; wherein the Sso7 domain comprises an amino acid sequence that (i) has at least 75% identity to SEQ ID NO:9, and (ii) has a substitute amino acid at a position, as determined with reference to SEQ ID NO:2, that is exposed on the surface of the Sso7 domain and interacts with the bases of a DNA double helix when the Sso7 domain is bound to DNA.

2. The Sso7 polymerase conjugate protein of claim 1, wherein the Sso7 domain comprises an amino acid sequence that has at least 90% identity to SEQ ID NO:9.

3. The Sso7 polymerase conjugate protein of claim 1, wherein the position is selected from the group consisting of a tryptophan residue at position 24, a valine residue at position 26, and a methionine residue at position 29.

4. The Sso7 polymerase conjugate protein of claim 3, wherein the position is a tryptophan residue at position 24, and the substitute amino acid residue is any amino acid other than aspartic acid, glutamic acid, arginine, lysine, or proline.

5. The Sso7 polymerase conjugate protein of claim 4, wherein the substitute amino acid residue is selected from the group consisting of glycine, valine, and alanine.

6. The Sso7 polymerase conjugate of claim 1, wherein the Sso7 domain is Sso7d, Sac7d, or Sac7e.

7. The Sso7 polymerase conjugate protein of claim 1, wherein the polymerase domain has thermally stable polymerase activity.

8. The Sso7 polymerase conjugate protein of claim 7, wherein the polymerase domain is a family A polymerase domain.

9. The Sso7 polymerase conjugate protein of claim 8, wherein the polymerase domain is a ΔTaq polymerase domain.

10. The Sso7 polymerase conjugate protein of claim 7, wherein the polymerase domain is a family B polymerase domain.

11. The Sso7 polymerase conjugate protein of claim 10, wherein the polymerase domain is from *Pyrococcus*.

12. A method of performing template-directed nucleic acid synthesis on a target nucleic acid present in a solution, the method comprising:
(a) contacting the target nucleic acid with an Sso7 polymerase conjugate protein of claim 1;
wherein the solution is of a composition that permits the Sso7 binding domain to bind to the target nucleic acid and the polymerase domain to extend a primer that is hybridized to the target nucleic acid sequence; and (b) incubating the solution under conditions in which the primer is extended by the polymerase.

13. The method of claim 12, wherein the position is selected from the group consisting of a tryptophan residue at position 24, a valine residue at position 26, and a methionine residue at position 29.

14. The method of claim 12, wherein the position is a tryptophan residue at position 24, and the replacement amino acid residue is any amino acid other than aspartic acid, glutamic acid, arginine, lysine, or proline.

15. The method of claim 14, wherein the substitute amino acid residue is selected from the group consisting of glycine, valine, and alanine.

16. The method of claim 12, wherein the Sso7 domain is Sso7d, Sac7d, or Sac7e.

17. The method of claim 12, wherein the polymerase domain has thermally stable polymerase activity.

* * * * *

SEQUENCE LISTING

<160> NUMBER OF SEQ ID NOS: 25

<210> SEQ ID NO 1
<211> LENGTH: 192
<212> TYPE: DNA
<213> ORGANISM: Sulfolobus solfataricus
<220> FEATURE:
<223> OTHER INFORMATION: Sso7d

<400> SEQUENCE: 1

```
atggcaaccg taaagttcaa gtacaaaggc gaagaaaaag aggtagacat ctccaagatc      60
aagaaagtat ggcgtgtggg caagatgatc tccttcacct acgacgaggg cggtggcaag     120
accggccgtg gtgcggtaag cgaaaaggac gcgccgaagg agctgctgca gatgctggag     180
aagcagaaaa ag                                                         192
```

<210> SEQ ID NO 2
<211> LENGTH: 64
<212> TYPE: PRT
<213> ORGANISM: Sulfolobus solfataricus
<220> FEATURE:
<223> OTHER INFORMATION: Sso7d protein

<400> SEQUENCE: 2

```
Met Ala Thr Val Lys Phe Lys Tyr Lys Gly Glu Glu Lys Glu Val Asp
  1               5                  10                  15

Ile Ser Lys Ile Lys Lys Val Trp Arg Val Gly Lys Met Ile Ser Phe
             20                  25                  30

Thr Tyr Asp Glu Gly Gly Gly Lys Thr Gly Arg Gly Ala Val Ser Glu
         35                  40                  45

Lys Asp Ala Pro Lys Glu Leu Leu Gln Met Leu Glu Lys Gln Lys Lys
     50                  55                  60
```

<210> SEQ ID NO 3
<211> LENGTH: 1907
<212> TYPE: DNA
<213> ORGANISM: Artificial Sequence
<220> FEATURE:
<223> OTHER INFORMATION: Description of Artificial
      Sequence:Sso7d(G)-deltaTaq substituted fusion
      polymerase

<400> SEQUENCE: 3

```
atgattacga attcgagcgc aaccgtaaag ttcaagtaca aaggcgaaga aaagaggta       60 gacatctcca agatcaagaa agtagggcgt gtgggcaaga tgatctcctt cacctacgac    120
gagggcggtg gcaagaccgg ccgtggtgcg gtaagcgaaa aggacgcgcc gaaggagctg    180
ctgcagatgc tggagaagca gaaaaagggc ggcggtgtca ctagtcccaa ggccctggag    240 gaggcccct ggccccgcc ggaagggggcc ttcgtgggct tgtgctttc ccgcaaggag      300 cccatgtggg ccgatcttct ggccctggcc gccgcagggg gggccgggt ccaccggcc      360 cccgagcctt ataaagccct cagggacctg aaggaggcgc ggggcttct cgccaaagac    420
```

```
ctgagcgttc tggccctgag ggaaggcctt ggcctcccgc ccggcgacga ccccatgctc      480
ctcgcctacc tcctggaccc ttccaacacc accccgagg gggtggcccg cgctacggc       540 ggggagtgga cggaggaggc ggggagcgg ccgcccttt ccgagaggct cttcgccaac       600
ctgtggggga ggcttgaggg ggaggagagg ctccttggc tttaccggga ggtggagagg      660 ccccttccg ctgtcctggc ccacatggag gccacgggg tgcgcctgga cgtggcctat       720
ctcagggcct tgtccctgga ggtggccgag gagatcgccc gcctcgaggc cgaggtcttc      780
cgcctggccg ccacccctt caacctcaac tcccgggacc agctggaaag ggtcctcttt       840
gacgagctag ggcttcccgc catcggcaag acggagaaga ccggcaagcg ctccaccagc      900
gccgccgtcc tggaggccct ccgcgaggcc accccatcg tggagaagat cctgcagtac      960
cgggagctca ccaagctgaa gagcacctac attgaccct tgccggacct catccacccc     1020
aggacgggcc gcctccacac ccgcttcaac cagacggcca cggccacggg caggctaagt    1080
agctccgatc ccaacctcca gaacatcccc gtccgcaccc cgcttgggca ggatccgc      1140 cgggccttca tcgccgagga ggggtggcta ttggtggccc tggactatag ccagatagag    1200
ctcagggtgc tggcccacct ctccggcgac gagaacctga tccgggtctt ccaggagggg    1260
cgggacatcc acacggagac cgccagctgg atgttcggcg tccccgggga ggccgtggac    1320
cccctgatgc gccgggcggc caagaccatc aacttcgggg tcctctacgg catgtcggcc    1380
caccgcctct cccaggagct agccatccct tacgaggagg cccaggcctt cattgagcgc    1440
tactttcaga gcttccccaa ggtgcgggcc tggattgaga gaccctgga ggagggcagg    1500 aggcgggggt acgtggagac cctcttcggc cgccgccgct acgtgccaga cctagaggcc    1560
cgggtgaaga gcgtgcggga ggcggccgag cgcatggcct tcaacatgcc cgtccagggc    1620
accgccgccg acctcatgaa gctggctatg gtgaagctct tccccaggct ggaggaaatg    1680
ggggccagga tgctccttca ggtccacgac gagctggtcc tcgaggcccc aaaagagagg    1740
gcggaggccg tggcccggct ggccaaggag gtcatggagg gggtgtatcc cctggccgtg    1800
cccctggagg tggaggtggg gatagggag gactggctct ccgccaagga gggcattgat    1860
ggccgcggcg gaggcgggca tcatcatcat catcattaat gagatct                  1907
```

<210> SEQ ID NO 4
<211> LENGTH: 632
<212> TYPE: PRT
<213> ORGANISM: Artificial Sequence
<220> FEATURE:
<223> OTHER INFORMATION: Description of Artificial
      Sequence:Sso7d(G)-deltaTaq substituted fusion
      polymerase protein

<400> SEQUENCE: 4

```
Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Gly Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Gly Val Thr Ser Pro Lys Ala Leu Glu
 65                  70                  75                  80

Glu Ala Pro Trp Pro Pro Pro Glu Gly Ala Phe Val Gly Phe Val Leu
                 85                  90                  95
```

```
Ser Arg Lys Glu Pro Met Trp Ala Asp Leu Leu Ala Leu Ala Ala Ala
            100                 105                 110

Arg Gly Gly Arg Val His Arg Ala Pro Glu Pro Tyr Lys Ala Leu Arg
            115                 120                 125

Asp Leu Lys Glu Ala Arg Gly Leu Leu Ala Lys Asp Leu Ser Val Leu
        130                 135                 140

Ala Leu Arg Glu Gly Leu Gly Leu Pro Gly Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
                180                 185                 190

Leu Ser Glu Arg Leu Phe Ala Asn Leu Trp Gly Arg Leu Glu Gly Glu
            195                 200                 205

Glu Arg Leu Leu Trp Leu Tyr Arg Glu Val Glu Arg Pro Leu Ser Ala
            210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Glu Ile Ala Arg Leu Glu
                245                 250                 255

Ala Glu Val Phe Arg Leu Ala Gly His Pro Phe Asn Leu Asn Ser Arg
            260                 265                 270

Asp Gln Leu Glu Arg Val Leu Phe Asp Glu Leu Gly Leu Pro Ala Ile
            275                 280                 285

Gly Lys Thr Glu Lys Thr Gly Lys Arg Ser Thr Ser Ala Ala Val Leu
            290                 295                 300

Glu Ala Leu Arg Glu Ala His Pro Ile Val Glu Lys Ile Leu Gln Tyr
305                 310                 315                 320

Arg Glu Leu Thr Lys Leu Lys Ser Thr Tyr Ile Asp Pro Leu Pro Asp
                325                 330                 335

Leu Ile His Pro Arg Thr Gly Arg Leu His Thr Arg Phe Asn Gln Thr
                340                 345                 350

Ala Thr Ala Thr Gly Arg Leu Ser Ser Ser Asp Pro Asn Leu Gln Asn
            355                 360                 365

Ile Pro Val Arg Thr Pro Leu Gly Gln Arg Ile Arg Arg Ala Phe Ile
        370                 375                 380

Ala Glu Glu Gly Trp Leu Leu Val Ala Leu Asp Tyr Ser Gln Ile Glu
385                 390                 395                 400

Leu Arg Val Leu Ala His Leu Ser Gly Asp Glu Asn Leu Ile Arg Val
                405                 410                 415

Phe Gln Glu Gly Arg Asp Ile His Thr Glu Thr Ala Ser Trp Met Phe
            420                 425                 430

Gly Val Pro Arg Glu Ala Val Asp Pro Leu Met Arg Arg Ala Ala Lys
            435                 440                 445

Thr Ile Asn Phe Gly Val Leu Tyr Gly Met Ser Ala His Arg Leu Ser
        450                 455                 460

Gln Glu Leu Ala Ile Pro Tyr Glu Glu Ala Gln Ala Phe Ile Glu Arg
465                 470                 475                 480

Tyr Phe Gln Ser Phe Pro Lys Val Arg Ala Trp Ile Glu Lys Thr Leu
                485                 490                 495

Glu Glu Gly Arg Arg Arg Gly Tyr Val Glu Thr Leu Phe Gly Arg Arg
            500                 505                 510

Arg Tyr Val Pro Asp Leu Glu Ala Arg Val Lys Ser Val Arg Glu Ala
```

```
                   515                 520                 525
Ala Glu Arg Met Ala Phe Asn Met Pro Val Gln Gly Thr Ala Ala Asp
            530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
                565                 570                 575

Pro Lys Glu Arg Ala Glu Ala Val Ala Arg Leu Ala Lys Glu Val Met
            580                 585                 590

Glu Gly Val Tyr Pro Leu Ala Val Pro Leu Glu Val Glu Val Gly Ile
                595                 600                 605

Gly Glu Asp Trp Leu Ser Ala Lys Glu Gly Ile Asp Gly Arg Gly Gly
            610                 615                 620

Gly Gly His His His His His His
625                 630

<210> SEQ ID NO 5
<211> LENGTH: 1907
<212> TYPE: DNA
<213> ORGANISM: Artificial Sequence
<220> FEATURE:
<223> OTHER INFORMATION: Description of Artificial
      Sequence:Sso7d(V)-deltaTaq substituted fusion
      polymerase

<400> SEQUENCE: 5
atgattacga attcgagcgc aaccgtaaag ttcaagtaca aaggcgaaga aaaagaggta        60
gacatctcca agatcaagaa agtagtgcgt gtgggcaaga tgatctcctt cacctacgac       120
gagggcggtg gcaagaccgg ccgtggtgcg gtaagcgaaa aggacgcgcc gaaggagctg       180
ctgcagatgc tggagaagca gaaaaagggc ggcggtgtca ctagtcccaa ggccctggag       240 gaggcccccct ggcccccgcc ggaagggcc ttcgtgggct tgtgctttc ccgcaaggag        300 cccatgtggg ccgatcttct ggccctggcc gccgccaggg ggcccgggt ccaccgggcc        360 cccgagcctt ataaagccct cagggacctg aaggaggcgc gggggcttct cgccaaagac       420
ctgagcgttc tggccctgag ggaaggcctt ggcctcccgc cggcgacga ccccatgctc        480 ctcgcctacc tcctggaccc ttccaacacc accccgagg ggtggcccg cgctacggc          540 ggggagtgga cggaggaggc gggggagcgg gccgcccttt ccgagaggct cttcgccaac       600 ctgtgggga ggcttgaggg ggaggagagg ctcctttggc tttaccggga ggtggagagg        660 ccccctttccg ctgtcctggc ccacatggag gccacggggg tgcgcctgga cgtggcctat       720
ctcagggcct gtcccctgga ggtggccgag gagatcgccc gcctcgaggc cgaggtcttc       780
cgcctggccg ccacccctt caacctcaac tcccgggacc agctggaaag ggtcctcttt        840
gacgagctag gcttcccgc catcggcaag acgagaaga ccggcaagcg ctccaccagc        900
gccgccgtcc tggaggccct ccgcgaggcc cacccatcg tggagaagat cctgcagtac       960
cgggagctca ccaagctgaa gagcacctac attgacccct gccggaccct catccacccc      1020
aggacgggcc gctccacac ccgcttcaac cagacgcca cggccacggg caggctaagt        1080
agctccgatc ccaacctcca gaacatcccc gtccgcaccc cgcttgggca gaggatccgc      1140
cgggccttca tcgccgagga ggggtggcta ttggtgccc tggactatag ccagatagag       1200
ctcagggtgc tggcccacct ctccggcgac gagaacctga tccgggtctt ccaggagggg      1260
cgggacatcc acacggagac cgccagctgg atgttcggcg tccccccgga ggccgtggac      1320
cccctgatgc gccggcggc caagaccatc aacttcgggg tcctctacgg catgtcggcc      1380
```

```
caccgcctct cccaggagct agccatccct tacgaggagg cccaggcctt cattgagcgc   1440
tactttcaga gcttccccaa ggtgcgggcc tggattgaga agaccctgga ggagggcagg   1500 aggcggggt acgtggagac cctcttcggc cgccgccgct acgtgccaga cctagaggcc    1560
cgggtgaaga gcgtgcggga ggcggccgag cgcatggcct tcaacatgcc cgtccagggc   1620
accgccgccg acctcatgaa gctggctatg gtgaagctct cccccaggct ggaggaaatg   1680
ggggccagga tgctccttca ggtccacgac gagctggtcc tcgaggcccc aaaagagagg   1740
gcggaggccg tggcccggct ggccaaggag gtcatggagg gggtgtatcc cctggccgtg   1800
cccctggagg tggaggtggg gatagggggag gactggctct ccgccaagga gggcattgat   1860
ggccgcggcg gaggcgggca tcatcatcat catcattaat gagatct                 1907
```

```
<210> SEQ ID NO 6
<211> LENGTH: 632
<212> TYPE: PRT
<213> ORGANISM: Artificial Sequence
<220> FEATURE:
<223> OTHER INFORMATION: Description of Artificial
      Sequence:Sso7d(V)-deltaTaq substituted fusion
      polymerase protein

<400> SEQUENCE: 6
```

```
Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Val Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Val Thr Ser Pro Lys Ala Leu Glu
 65                  70                  75                  80

Glu Ala Pro Trp Pro Pro Glu Gly Ala Phe Val Gly Phe Val Leu
                 85                  90                  95

Ser Arg Lys Glu Pro Met Trp Ala Asp Leu Leu Ala Leu Ala Ala Ala
            100                 105                 110

Arg Gly Gly Arg Val His Arg Ala Pro Glu Pro Tyr Lys Ala Leu Arg
        115                 120                 125

Asp Leu Lys Glu Ala Arg Gly Leu Leu Ala Lys Asp Leu Ser Val Leu
    130                 135                 140

Ala Leu Arg Glu Gly Leu Gly Leu Pro Pro Gly Asp Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
            180                 185                 190

Leu Ser Glu Arg Leu Phe Ala Asn Leu Trp Gly Arg Leu Glu Gly Glu
        195                 200                 205

Glu Arg Leu Leu Trp Leu Tyr Arg Glu Val Glu Arg Pro Leu Ser Ala
    210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Glu Ile Ala Arg Leu Glu
                245                 250                 255

Ala Glu Val Phe Arg Leu Ala Gly His Pro Phe Asn Leu Asn Ser Arg
```

```
                    260                 265                 270
Asp Gln Leu Glu Arg Val Leu Phe Asp Glu Leu Gly Leu Pro Ala Ile
                275                 280                 285
Gly Lys Thr Glu Lys Thr Gly Lys Arg Ser Thr Ser Ala Ala Val Leu
            290                 295                 300
Glu Ala Leu Arg Glu Ala His Pro Ile Val Glu Lys Ile Leu Gln Tyr
305                 310                 315                 320
Arg Glu Leu Thr Lys Leu Lys Ser Thr Tyr Ile Asp Pro Leu Pro Asp
                325                 330                 335
Leu Ile His Pro Arg Thr Gly Arg Leu His Thr Arg Phe Asn Gln Thr
            340                 345                 350
Ala Thr Ala Thr Gly Arg Leu Ser Ser Ser Asp Pro Asn Leu Gln Asn
            355                 360                 365
Ile Pro Val Arg Thr Pro Leu Gly Gln Arg Ile Arg Arg Ala Phe Ile
        370                 375                 380
Ala Glu Glu Gly Trp Leu Leu Val Ala Leu Asp Tyr Ser Gln Ile Glu
385                 390                 395                 400
Leu Arg Val Leu Ala His Leu Ser Gly Asp Glu Asn Leu Ile Arg Val
                405                 410                 415
Phe Gln Glu Gly Arg Asp Ile His Thr Glu Thr Ala Ser Trp Met Phe
            420                 425                 430
Gly Val Pro Arg Glu Ala Val Asp Pro Leu Met Arg Arg Ala Ala Lys
            435                 440                 445
Thr Ile Asn Phe Gly Val Leu Tyr Gly Met Ser Ala His Arg Leu Ser
450                 455                 460
Gln Glu Leu Ala Ile Pro Tyr Glu Glu Ala Gln Ala Phe Ile Glu Arg
465                 470                 475                 480
Tyr Phe Gln Ser Phe Pro Lys Val Arg Ala Trp Ile Glu Lys Thr Leu
                485                 490                 495
Glu Glu Gly Arg Arg Gly Tyr Val Glu Thr Leu Phe Gly Arg Arg
            500                 505                 510
Arg Tyr Val Pro Asp Leu Glu Ala Arg Val Lys Ser Val Arg Glu Ala
            515                 520                 525
Ala Glu Arg Met Ala Phe Asn Met Pro Val Gln Gly Thr Ala Ala Asp
        530                 535                 540
Leu Met Lys Leu Ala Met Val Lys Leu Phe Pro Arg Leu Glu Glu Met
545                 550                 555                 560
Gly Ala Arg Met Leu Leu Gln Val His Asp Glu Leu Val Leu Glu Ala
                565                 570                 575
Pro Lys Glu Arg Ala Glu Ala Val Ala Arg Leu Ala Lys Glu Val Met
            580                 585                 590
Glu Gly Val Tyr Pro Leu Ala Val Pro Leu Glu Val Glu Val Gly Ile
        595                 600                 605
Gly Glu Asp Trp Leu Ser Ala Lys Glu Gly Ile Asp Gly Arg Gly Gly
        610                 615                 620
Gly Gly His His His His His His
625                 630

<210> SEQ ID NO 7
<211> LENGTH: 1907
<212> TYPE: DNA
<213> ORGANISM: Artificial Sequence
<220> FEATURE:
<223> OTHER INFORMATION: Description of Artificial
      Sequence:Sso7d(E)-deltaTaq substituted fusion
      polymerase
```

<400> SEQUENCE: 7

```
atgattacga attcgagcgc aaccgtaaag ttcaagtaca aaggcgaaga aaaagaggta      60
gacatctcca agatcaagaa agtagagcgt gtgggcaaga tgatctcctt cacctacgac     120
gagggcggtg gcaagaccgg ccgtggtgcg gtaagcgaaa aggacgcgcc gaaggagctg     180
ctgcagatgc tggagaagca gaaaaagggc ggcggtgtca ctagtcccaa ggccctggag     240
gaggccccct ggccccgcc ggaagggggcc ttcgtgggct tgtgctttc ccgcaaggag      300
ccatgtggg ccgatcttct ggccctggcc gccgccaggg ggggccgggt ccaccgggcc      360
cccgagcctt ataaagccct cagggacctg aaggaggcgc gggggcttct cgccaaagac    420
ctgagcgttc tggccctgag ggaaggcctt ggcctcccgc ccggcgacga ccccatgctc    480
ctcgcctacc tcctggaccc ttccaacacc accccgagg gggtggcccg cgctacggc      540
ggggagtgga cggaggaggc ggggagcgg gccgcccttt ccgagaggct cttcgccaac     600
ctgtgggga ggcttgaggg ggaggagagg ctccttggc tttaccggga ggtggagagg      660
cccctttccg ctgtcctggc ccacatggag gccacggggg tgcgcctgga cgtggcctat    720
ctcagggcct tgtccctgga ggtggccgag gagatcgccc gctcgaggc cgaggtcttc    780
cgcctggccg ccaccccttt aacctcaac tccgggaccc agctggaaag ggtcctcttt    840
gacgagctag gcttcccgc catcggcaag acggagaaga ccggcaagcg ctccaccagc    900
ccgccgtcc tggaggccct ccgcgaggcc cacccatcg tggagaagat cctgcagtac    960
cgggagctca ccaagctgaa gagcacctac attgacccct gccggaccct catccacccc   1020
aggacgggcc gctccacac ccgcttcaac cagacggcca cggccacggg caggctaagt    1080
agctccgatc ccaacctcca gaacatcccc gtccgcaccc cgcttgggca ggatccgc      1140
cgggccttca tcgccgagga ggggtggcta ttggtggccc tggactatag ccagatagag    1200
ctcagggtgc tggcccacct ctccggcgac gagaacctga tccgggtctt caggagggg    1260
cgggacatcc acacggagac cgccagctgg atgttcggcg tccccggga ggccgtggac    1320
cccctgatgc gcgggcggc caagaccatc aacttcgggg tcctctacgg catgtcggcc    1380
caccgcctct cccaggagct agccatccct tacgaggagg cccaggcctt cattgagcgc    1440
tactttcaga gcttcccaa ggtgcgggcc tggattgaga gacccctgga ggagggcagg    1500
aggcggggt acgtggagac cctcttcggc cgccgccgct acgtgccaga cctagaggcc    1560
cgggtgaaga gcgtgcggga ggcggccgag cgcatggcct tcaacatgcc cgtccagggc    1620
accgccgccg acctcatgaa gctggctatg gtgaagctct cccccaggct ggaggaaatg    1680
ggggccagga tgctccttca ggtccacgac gagctggtcc tcgaggcccc aaaagagagg    1740
gcggaggccg tggcccggct ggccaaggag gtcatggagg gggtgtatcc cctggccgtg    1800
cccctggagg tggaggtggg gataggggag gactggctct ccgccaagga gggcattgat    1860
ggccgcggcg gaggcgggca tcatcatcat catcattaat gagatct                  1907
```

<210> SEQ ID NO 8
<211> LENGTH: 632
<212> TYPE: PRT
<213> ORGANISM: Artificial Sequence
<220> FEATURE:
<223> OTHER INFORMATION: Description of Artificial
      Sequence:Sso7d(E)-deltaTaq substituted fusion
      polymerase protein

<400> SEQUENCE: 8

Met Ile Thr Asn Ser Ser Ala Thr Val Lys Phe Lys Tyr Lys Gly Glu

-continued

```
  1               5               10              15
Glu Lys Glu Val Asp Ile Ser Lys Ile Lys Lys Val Glu Arg Val Gly
             20                  25                  30

Lys Met Ile Ser Phe Thr Tyr Asp Glu Gly Gly Lys Thr Gly Arg
             35                  40              45

Gly Ala Val Ser Glu Lys Asp Ala Pro Lys Glu Leu Leu Gln Met Leu
         50                  55                  60

Glu Lys Gln Lys Lys Gly Gly Val Thr Ser Pro Lys Ala Leu Glu
 65                  70                  75                  80

Glu Ala Pro Trp Pro Pro Glu Gly Ala Phe Val Gly Phe Val Leu
                 85                  90                  95

Ser Arg Lys Glu Pro Met Trp Ala Asp Leu Leu Ala Leu Ala Ala
                100                 105                 110

Arg Gly Gly Arg Val His Arg Ala Pro Glu Pro Tyr Lys Ala Leu Arg
             115                 120                 125

Asp Leu Lys Glu Ala Arg Gly Leu Leu Ala Lys Asp Leu Ser Val Leu
         130                 135                 140

Ala Leu Arg Glu Gly Leu Gly Leu Pro Pro Gly Asp Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
                180                 185                 190

Leu Ser Glu Arg Leu Phe Ala Asn Leu Trp Gly Arg Leu Glu Gly Glu
             195                 200                 205

Glu Arg Leu Leu Trp Leu Tyr Arg Glu Val Glu Arg Pro Leu Ser Ala
         210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Ile Ala Arg Leu Glu
                245                 250                 255

Ala Glu Val Phe Arg Leu Ala Gly His Pro Phe Asn Leu Asn Ser Arg
                260                 265                 270

Asp Gln Leu Glu Arg Val Leu Phe Asp Glu Leu Gly Leu Pro Ala Ile
             275                 280                 285

Gly Lys Thr Glu Lys Thr Gly Lys Arg Ser Thr Ser Ala Ala Val Leu
         290                 295                 300

Glu Ala Leu Arg Glu Ala His Pro Ile Val Glu Lys Ile Leu Gln Tyr
305                 310                 315                 320

Arg Glu Leu Thr Lys Leu Lys Ser Thr Tyr Ile Asp Pro Leu Pro Asp
                325                 330                 335

Leu Ile His Pro Arg Thr Gly Arg Leu His Thr Arg Phe Asn Gln Thr
                340                 345                 350

Ala Thr Ala Thr Gly Arg Leu Ser Ser Asp Pro Asn Leu Gln Asn
             355                 360                 365

Ile Pro Val Arg Thr Pro Leu Gly Gln Arg Ile Arg Arg Ala Phe Ile
         370                 375                 380

Ala Glu Glu Gly Trp Leu Leu Val Ala Leu Asp Tyr Ser Gln Ile Glu
385                 390                 395                 400

Leu Arg Val Leu Ala His Leu Ser Gly Asp Glu Asn Leu Ile Arg Val
                405                 410                 415

Phe Gln Glu Gly Arg Asp Ile His Thr Glu Thr Ala Ser Trp Met Phe
             420                 425                 430
```

Gly Val Pro Arg Glu Ala Val Asp Pro Leu Met Arg Arg Ala Ala Lys
        435                 440                 445

Thr Ile Asn Phe Gly Val Leu Tyr Gly Met Ser Ala His Arg Leu Ser
450                 455                 460

Gln Glu Leu Ala Ile Pro Tyr Glu Ala Gln Ala Phe Ile Glu Arg
465                 470                 475                 480

Tyr Phe Gln Ser Phe Pro Lys Val Arg Ala Trp Ile Glu Lys Thr Leu
                485                 490                 495

Glu Glu Gly Arg Arg Gly Tyr Val Glu Thr Leu Phe Gly Arg Arg
                500                 505                 510

Arg Tyr Val Pro Asp Leu Glu Ala Arg Val Lys Ser Val Arg Glu Ala
        515                 520                 525

Ala Glu Arg Met Ala Phe Asn Met Pro Val Gln Gly Thr Ala Ala Asp
530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
                565                 570                 575

Pro Lys Glu Arg Ala Glu Ala Val Ala Arg Leu Ala Lys Glu Val Met
                580                 585                 590

Glu Gly Val Tyr Pro Leu Ala Val Pro Leu Glu Val Glu Val Gly Ile
        595                 600                 605

Gly Glu Asp Trp Leu Ser Ala Lys Glu Gly Ile Asp Gly Arg Gly Gly
        610                 615                 620

Gly Gly His His His His His
625                 630

<210> SEQ ID NO 9
<211> LENGTH: 63
<212> TYPE: PRT
<213> ORGANISM: Sulfolobus solfataricus
<220> FEATURE:
<223> OTHER INFORMATION: Sso7d with start methionine not shown

<400> SEQUENCE: 9

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 10
<211> LENGTH: 64
<212> TYPE: PRT
<213> ORGANISM: Sulfolobus acidocaldarius
<220> FEATURE:
<223> OTHER INFORMATION: Sso7d-like protein Sac7e

<400> SEQUENCE: 10

Ala Lys Val Arg Phe Lys Tyr Lys Gly Glu Glu Lys Glu Val Asp Thr
1               5                   10                  15

Ser Lys Ile Lys Lys Val Trp Arg Val Gly Lys Met Val Ser Phe Thr
            20                  25                  30

Tyr Asp Asp Asn Gly Lys Thr Gly Arg Gly Ala Val Ser Glu Lys Asp
        35                  40                  45

```
Ala Pro Lys Glu Leu Met Asp Met Leu Ala Arg Ala Glu Lys Lys Lys
        50                  55                  60

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence:Sso7d and
      Sac7e alignment consensus peptide

<400> SEQUENCE: 11

Val Lys Phe Lys Tyr Lys Gly Glu Glu Lys Glu Val Asp
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence:Sso7d and
      Sac7e alignment consensus peptide

<400> SEQUENCE: 12

Ser Lys Ile Lys Lys Val Trp Arg Val Gly Lys Met
 1               5                  10

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:Sso7d and
      Sac7e alignment consensus peptide

<400> SEQUENCE: 13

Ser Phe Thr Tyr Asp
 1               5

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence:Sso7d and
      Sac7e alignment consensus peptide

<400> SEQUENCE: 14

Gly Gly Gly Lys Thr Gly Arg Gly Ala Val Ser Glu Lys Asp Ala Pro
 1               5                  10                  15

Lys Glu Leu

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:forward
      amplification primer

<400> SEQUENCE: 15
gcaacagtaa agttcaagta caaagg                                           26

<210> SEQ ID NO 16
<211> LENGTH: 29
<212> TYPE: DNA
<213> ORGANISM: Artificial Sequence
<220> FEATURE:
```

-continued

```
<223> OTHER INFORMATION: Description of Artificial Sequence:reverse
      amplification primer

<400> SEQUENCE: 16
ctaacatttg tagtagttct tttggagcg                                           29

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 17

His His His His His His
  1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:
      anti-DYKDDDDK epitope tag

<400> SEQUENCE: 18

Asp Tyr Lys Asp Asp Asp Asp Lys
  1               5

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:sequential
      PCR first round amplification primer M13R

<400> SEQUENCE: 19
gcggataaca atttcacaca gg                                                  22

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence:sequential
      PCR first round amplification primer W24T
<220> FEATURE:
<221> NAME/KEY: modified_base
<222> LOCATION: (23)
<223> OTHER INFORMATION: n = g, a, c or t

<400> SEQUENCE: 20
atctccaaga tcaagaaagt agngcgtgtg ggcaagatg                                39

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:sequential
      PCR first round amplification primer W24AEVG-B

<400> SEQUENCE: 21
ctactttctt gatcttggag at                                                  22

<210> SEQ ID NO 22
```

```
<211> LENGTH: 19
<212> TYPE: DNA
<213> ORGANISM: Artificial Sequence
<220> FEATURE:
<223> OTHER INFORMATION: Description of Artificial Sequence:sequential
      PCR first round amplification primer 1008R

<400> SEQUENCE: 22
gagggcttta taaggctcg                                                  19

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:matched
      primer 57F

<400> SEQUENCE: 23
tccgttcttc ttcgtcataa ct                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:mismatched
      primer 57F5/6

<400> SEQUENCE: 24
tccgcccttc ttcgtcataa ct                                              22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:matched
      reverse primer 732R

<400> SEQUENCE: 25
cctgactgtt cgatatattc actc                                            24
```